(12) United States Patent
Mahrouche et al.

(10) Patent No.: US 10,687,882 B2
(45) Date of Patent: Jun. 23, 2020

(54) $N_2O$ THERMAL PRESSURIZATION SYSTEM BY COOLING

(71) Applicant: Medtronic CryoCath LP, Toronto (CA)

(72) Inventors: Rachid Mahrouche, La Salle (CA); Eric Monger, Beloeil (CA)

(73) Assignee: Medtronic CryoCath LP, Toronto, Ontario ( * ) Notice: Subject to any disclaimer, the term of this patent is extended or adjusted under 35 U.S.C. 154(b) by 140 days.

(21) Appl. No.: 15/922,497

(22) Filed: Mar. 15, 2018

(65) Prior Publication Data
US 2018/0199979 A1   Jul. 19, 2018

Related U.S. Application Data

(62) Division of application No. 14/790,465, filed on Jul. 2, 2015, now Pat. No. 9,993,280.

(51) Int. Cl.
*F25B 13/00* (2006.01)
*A61B 18/02* (2006.01)
*F25J 1/02* (2006.01)

(52) U.S. Cl.
CPC .............. *A61B 18/02* (2013.01); *F25B 13/00* (2013.01); *F25J 1/0204* (2013.01)

(58) Field of Classification Search
CPC .......... A61B 18/02; F25J 1/0204; F25B 13/00
See application file for complete search history.

(56) References Cited

U.S. PATENT DOCUMENTS 3,722,581 A * 3/1973 Sauer ................... F25J 5/002
165/96
3,729,946 A * 5/1973 Massey ................ F17C 9/00
62/50.1

(Continued)

FOREIGN PATENT DOCUMENTS

EP    1980287 A2   10/2008
EP    2387964 A2   11/2011
(Continued)

OTHER PUBLICATIONS

International Search Report and Written Opinion dated Jun. 30, 2016, for corresponding International Application No. PCT/CA2016/050669; International Filing Date: Jun. 10, 2016 consisting of 7 pages.

(Continued)

*Primary Examiner* — David J Teitelbaum
(74) *Attorney, Agent, or Firm* — Christopher & Weisberg, P.A.

(57) ABSTRACT

A system and method of using a source of low-pressure refrigerant for a cryotherapy procedure. The system may generally include a fluid reservoir and a fluid flow path in thermal exchange with the fluid reservoir, the fluid flow path including a thermal exchange device in thermal exchange with the fluid reservoir, a compressor in fluid communication with the thermal exchange device, a condenser, a reversing valve located between the compressor and the condenser, and an expansion valve located between the condenser and the thermal exchange device. The method may include transferring a low-pressure refrigerant to a first fluid reservoir, reducing the temperature of the refrigerant within the first fluid reservoir, increasing the temperature of the refrigerant within the first fluid reservoir, and transfer- (Continued)

ring the pressurized refrigerant from the first fluid reservoir to a second fluid reservoir.

12 Claims, 3 Drawing Sheets

(56) References Cited

U.S. PATENT DOCUMENTS

| | | | |
|---|---|---|---|
| 4,653,287 A * | 3/1987 | Martin, Jr. | F24D 11/0214 62/181 |
| 5,860,971 A * | 1/1999 | Clarke | A61B 18/02 606/20 |
| 6,270,493 B1 | 8/2001 | Lalonde et al. | |
| 6,306,129 B1 | 10/2001 | Little | |
| 6,575,966 B2 | 6/2003 | Lane et al. | |
| 7,004,936 B2 | 2/2006 | Ryba et al. | |
| 7,300,433 B2 | 11/2007 | Lane et al. | |
| 7,527,622 B2 | 5/2009 | Lane et al. | |
| 7,648,497 B2 | 1/2010 | Lane et al. | |
| 7,727,228 B2 | 6/2010 | Abboud et al. | |
| 7,740,627 B2 | 6/2010 | Gammie et al. | |
| 7,794,455 B2 | 9/2010 | Abboud et al. | |
| 7,871,395 B2 | 1/2011 | Hu et al. | |
| 8,298,217 B2 | 10/2012 | Lane et al. | |
| 8,382,747 B2 | 2/2013 | Abboud et al. | |
| 2004/0243119 A1 | 12/2004 | Lane et al. | |
| 2005/0215989 A1 | 9/2005 | Abboud et al. | |
| 2006/0030843 A1 | 2/2006 | Lane et al. | |
| 2006/0122589 A1 | 6/2006 | Abboud et al. | |
| 2007/0032783 A1 | 2/2007 | Abboud et al. | |
| 2008/0009925 A1 | 1/2008 | Abboud et al. | |
| 2008/0039791 A1 | 2/2008 | Abboud et al. | |
| 2008/0091180 A1 | 4/2008 | Abboud et al. | |
| 2008/0097373 A1 | 4/2008 | Hu et al. | |
| 2008/0097421 A1 | 4/2008 | Hu et al. | |
| 2008/0103493 A1 | 5/2008 | Abboud et al. | |
| 2008/0114344 A1 * | 5/2008 | Xiao | A61B 18/02 606/20 |
| 2008/0215043 A1 | 9/2008 | Abboud et al. | |
| 2009/0088735 A1 | 4/2009 | Abboud et al. | |
| 2009/0182318 A1 | 7/2009 | Abboud et al. | |
| 2009/0182319 A1 | 7/2009 | Lane et al. | |
| 2009/0299356 A1 | 12/2009 | Watson | |
| 2011/0184400 A1 | 7/2011 | Pageard | |
| 2012/0089047 A1 | 4/2012 | Ryba et al. | |
| 2012/0109115 A1 | 5/2012 | Condie et al. | |
| 2012/0109119 A1 | 5/2012 | Lalonde | |
| 2012/0130359 A1 | 5/2012 | Turovskiy | |
| 2012/0130360 A1 | 5/2012 | Buckley et al. | |
| 2012/0130458 A1 | 5/2012 | Ryba et al. | |
| 2012/0136344 A1 | 5/2012 | Buckley et al. | |
| 2012/0136417 A1 | 5/2012 | Buckley et al. | |
| 2012/0136418 A1 | 5/2012 | Buckley et al. | |
| 2012/0143294 A1 | 6/2012 | Clark et al. | |
| 2012/0150267 A1 | 6/2012 | Buckley et al. | |
| 2012/0158104 A1 | 6/2012 | Huynh et al. | |
| 2012/0245574 A1 | 9/2012 | Lalonde | |
| 2012/0253336 A1 | 10/2012 | Littrup et al. | |
| 2013/0345688 A1 | 12/2013 | Babkin et al. | |

FOREIGN PATENT DOCUMENTS

| | | |
|---|---|---|
| WO | 2003020334 A2 | 3/2003 |
| WO | 2005089853 A1 | 9/2005 |
| WO | 2006017073 A2 | 2/2006 |
| WO | 2006118725 A1 | 11/2006 |
| WO | 2006124176 A1 | 11/2006 |
| WO | 2008046183 A1 | 4/2008 |
| WO | 2010081221 A1 | 7/2010 |
| WO | 2011091507 A1 | 8/2011 |
| WO | 2012019156 A1 | 2/2012 |
| WO | 2012057911 A1 | 5/2012 |
| WO | 2012058156 A1 | 5/2012 |
| WO | 2012058158 A1 | 5/2012 |
| WO | 2012058160 A1 | 5/2012 |
| WO | 2012058167 A1 | 5/2012 |
| WO | 2012129646 A1 | 10/2012 |

OTHER PUBLICATIONS

Supplementary European Search Report and Search Opinion dated Jan. 24, 2019 for European Application No. 16816882 filed on Jan. 3, 2018; Consisting of 2 pages.

* cited by examiner

N₂O THERMAL PRESSURIZATION SYSTEM BY COOLING

CROSS-REFERENCE TO RELATED APPLICATION

This application is a divisional of and claims priority to patent application Ser. No. 14/790,465, filed Jul. 2, 2015, entitled N2O THERMAL PRESSURIZATION SYSTEM BY COOLING, the entirety of which is incorporated herein by reference.

STATEMENT REGARDING FEDERALLY SPONSORED RESEARCH OR DEVELOPMENT n/a

TECHNICAL FIELD

The present invention relates to a system and method of using a source of low-pressure refrigerant for a cryotherapy procedure. Specifically, the present invention relates to a system and method of pressurizing a source of low-pressure refrigerant by manipulating the temperature of the refrigerant.

BACKGROUND

Cryotherapy includes variety of techniques used to treat and/or map tissue, and is commonly used for procedures involving cardiac tissue. Certain types of cryotherapy, such as cryoablation, involves the use of pressurized refrigerant, which is allowed to expand within, and thereby cool tissue adjacent to, the distal portion of the treatment device. The pressurized refrigerant is typically stored in a pressurized tank or cylinder in the console of the system. Although the tank is easily removed and replaced when the refrigerant source runs out, it would be more economical to refill the tank with a new supply of refrigerant. Additionally, the pressurized tanks are considered to be Dangerous Goods, and it would therefore be desirable to reduce the amount of transport, handling, and storage of refrigerant tanks used for cryotherapy procedures.

Many medical facilities, especially hospitals, include a native or in-facility, integrated source of nitrous oxide (N₂O), which is commonly used as an anesthetic. Nitrous oxide may also be used as a refrigerant in cryotherapy systems. However, the native nitrous oxide is typically stored at approximately 50 psig, which is considered a low-pressure environment. At this pressure, the nitrous oxide is unsuitable for use in a cryotherapy system and must first be pressurized and safely transferred to the cryotherapy system refrigerant reservoir. The low-pressure refrigerant cannot be used in a cryotherapy system if the refrigerant is simply compressed, since the refrigerant must also be cooled to a temperature suitable for use in the cryotherapy system.

It is therefore desirable to provide a method and system for pressurizing a low-pressure source of refrigerant and safely transferring the pressurized refrigerant to a cryotherapy system. It is further desirable to provide a refrigerant delivery system that includes a pressurization system that provides an interface between a low-pressure refrigerant source and a cryotherapy system.

SUMMARY

The present invention advantageously provides a method and system for using a source of low-pressure refrigerant for a cryotherapy procedure. The system or kit for use with a source of low-pressure refrigerant may generally include a fluid reservoir and a closed-loop fluid flow path in thermal exchange with the fluid reservoir, the closed-loop fluid flow path including: a thermal exchange device in thermal exchange with and fluidly isolated from the fluid reservoir; a compressor in fluid communication with the thermal exchange device; a condenser; a reversing valve located between the compressor and the condenser; and an expansion valve located between the condenser and the thermal exchange device. The fluid reservoir and the thermal exchange device may be located in an insulating container. Further, the thermal exchange device may be coiled around at least a portion of the fluid reservoir and the thermal exchange device may be immersed in a non-freezing liquid within the insulating container. The fluid flow path may be a first fluid flow path, and the kit may further include a second fluid flow path, with the fluid reservoir being included in the second fluid flow path. The fluid reservoir may be configured to receive low-pressure refrigerant from the source of low-pressure refrigerant, and the kit may be configured to pressurize the low-pressure refrigerant by adjusting the temperature of the low-pressure refrigerant. The fluid reservoir may be a first fluid reservoir and the kit may further include a second fluid reservoir in the second fluid flow path, with the kit being configured to transfer pressurized refrigerant from the first fluid reservoir to the second fluid reservoir. The first fluid path may contain a secondary refrigerant. Further, the reversing valve may be configured to selectively allow circulation of the secondary refrigerant in one of a first direction and a second direction. The first fluid flow path may further include a first three-way valve located between the reversing valve and the condenser, the first three-way valve being configured to transfer the secondary refrigerant: to the condenser when the reversing valve allows circulation of the secondary refrigerant in the first direction; and to the compressor when the reversing valve allows circulation of the secondary refrigerant in the second direction. The second fluid reservoir may be in thermal exchange with a second thermal exchange device, with the first fluid flow path further including a second three-way valve located between the condenser and the expansion valve, the second three-way valve being configured to transfer the secondary refrigerant: to the expansion valve when the reversing valve allows circulation of the secondary refrigerant in the first direction; and to the second thermal exchange device when the reversing valve allows circulation of the secondary refrigerant in the second direction. The second fluid flow path may further include a vacuum source located downstream of the first fluid reservoir.

A system or kit for use with a source of low-pressure refrigerant and a cryotherapy system may generally include: a first fluid flow path and a closed-loop second fluid flow path. The first fluid flow path may include: a first fluid reservoir configured to receive a low-pressure refrigerant from the low-pressure refrigerant source; and a second fluid reservoir configured to receive a pressurized refrigerant from the first fluid reservoir. The closed-loop second fluid flow path may include: a first thermal exchange device in thermal exchange with the first fluid reservoir; a second thermal exchange device in thermal exchange with the second fluid reservoir; a compressor in fluid communication with the first thermal exchange device; a condenser; a reversing valve located between the compressor and the condenser, the reversing valve being configured to selectively allow circulation of the secondary refrigerant in one of a first direction and a second direction; a first three-way valve located between the reversing valve and the condenser; a second three-way valve located between the condenser and the expansion valve; and an expansion valve located between the condenser and the first thermal exchange device. The first three-way valve may be configured to transfer the secondary refrigerant to the condenser when the reversing valve allows circulation of the secondary refrigerant in the first direction, and the first three-way valve being configured to transfer the secondary refrigerant to the compressor when the reversing valve allows circulation of the secondary refrigerant in the second direction, and the second three-way valve may be configured to transfer the secondary refrigerant to the expansion valve when the reversing valve allows circulation of the secondary refrigerant in the first direction, and the second three-way valve being configured to transfer the secondary refrigerant to the second thermal exchange device when the reversing valve allows circulation of the secondary refrigerant in the second direction. Circulation of the secondary refrigerant in the first direction may reduce the temperature of the low-pressure refrigerant within the first fluid reservoir. Conversely, circulation of the secondary refrigerant in the second direction may increase the temperature and the pressure of the low-pressure refrigerant within the first fluid reservoir.

A method of transferring a low-pressure refrigerant from a low-pressure refrigerant source to a cryotherapy system may generally include: transferring a low-pressure refrigerant to a first fluid reservoir; reducing the temperature of the low-pressure refrigerant within the first fluid reservoir; increasing the temperature of the low-pressure refrigerant within the first fluid reservoir, increasing the temperature of the low-pressure refrigerant causing the pressure of the low-pressure refrigerant to increase; and transferring the pressurized refrigerant from the first fluid reservoir to a second fluid reservoir. The low-pressure refrigerant may be transferred to the first fluid reservoir within a first fluid flow path, and reducing the temperature of the low-pressure refrigerant within the first fluid reservoir may include circulating a secondary refrigerant in a first direction within a second fluid flow path that is in thermal exchange with the first fluid flow path. Increasing the temperature of the low-pressure refrigerant within the first fluid reservoir may include circulating the secondary refrigerant in a second direction within the second fluid flow path. The pressurized refrigerant may be transferred within the first fluid flow path from the first fluid reservoir to the second fluid reservoir, and circulating the secondary refrigerant in the second direction within the second fluid flow path may both increase the temperature of the low-pressure refrigerant within the first fluid reservoir and decrease the temperature of the pressurized refrigerant within the second fluid reservoir.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
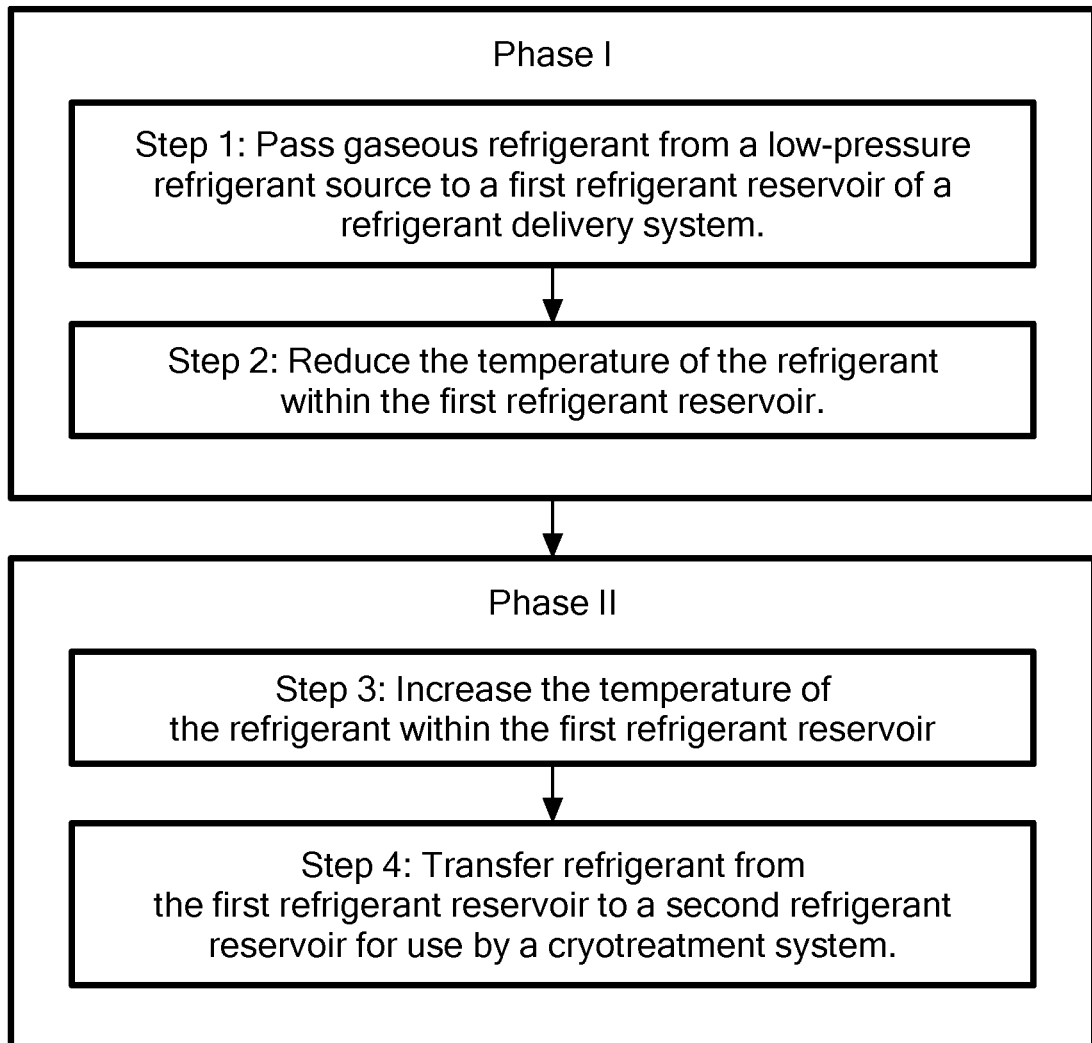
FIG. 1 shows a flow chart for a method of refrigerant delivery from a low-pressure, native refrigerant source to a cryotherapy system.
Figure 2:
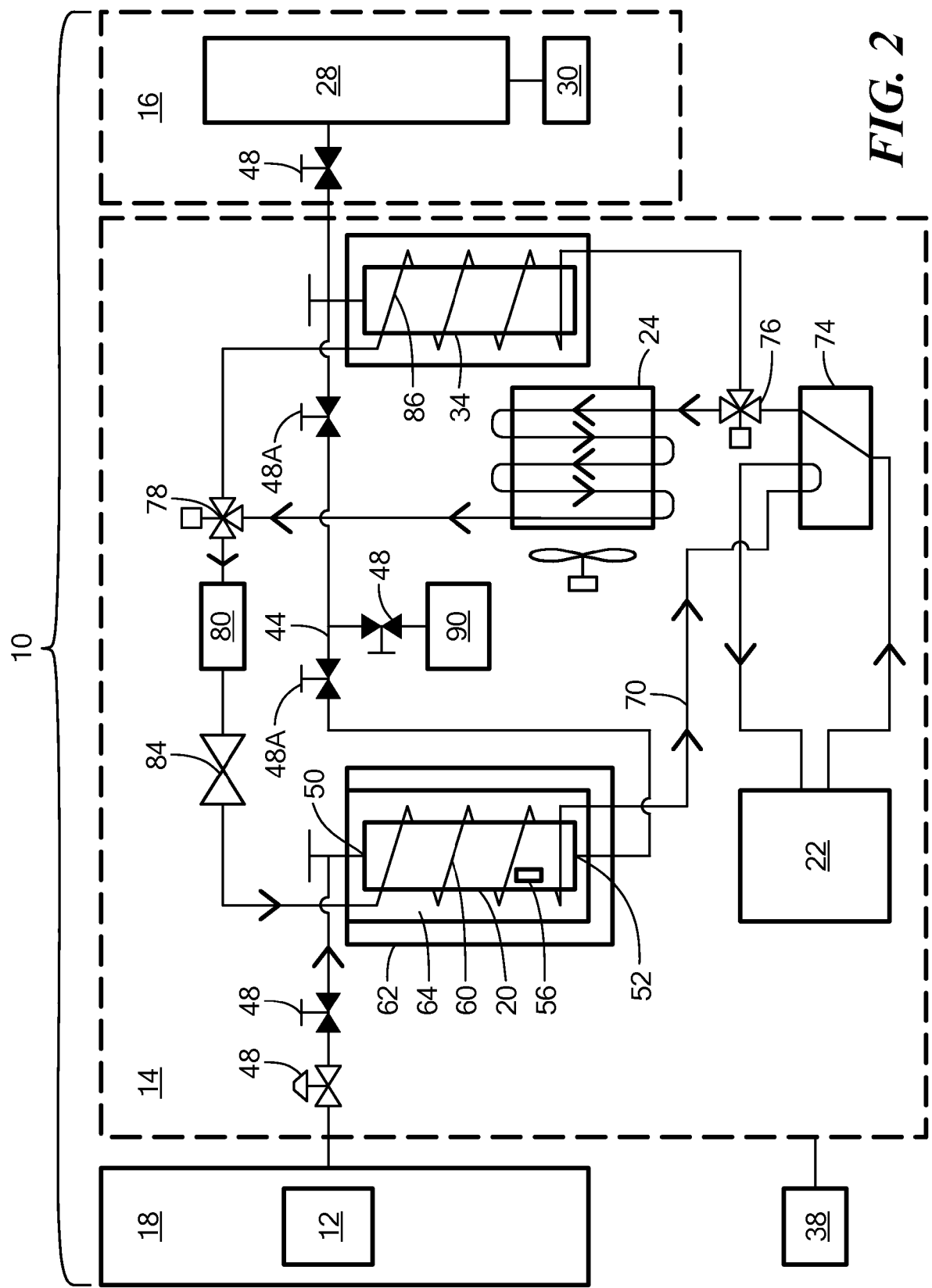
FIG. 2 shows a schematic representation of a refrigerant delivery system, with a secondary refrigerant flowing through a fluid flow path in a first direction.
Figure 3:
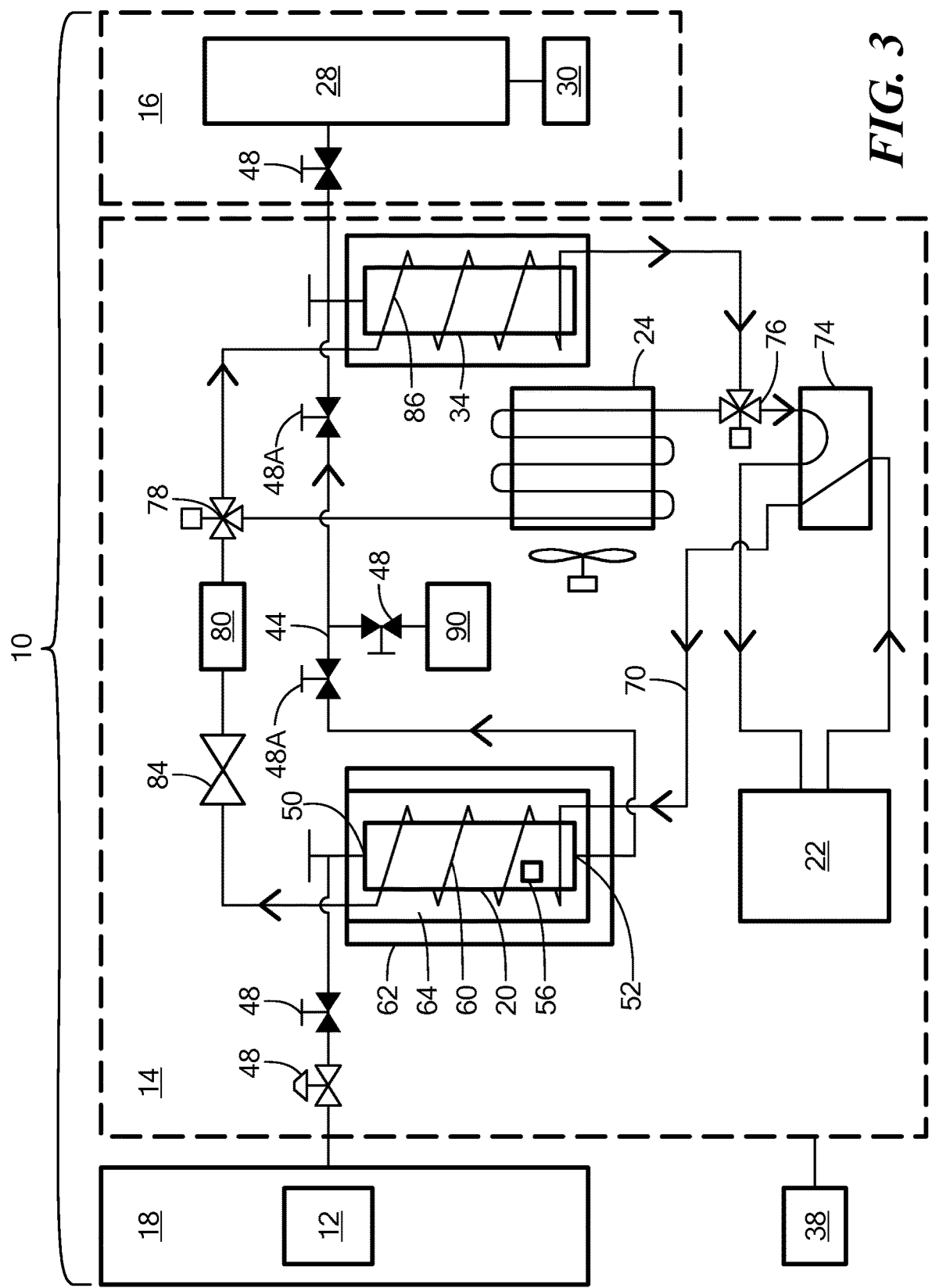
FIG. 3 shows a schematic representation of the refrigerant delivery system, with a secondary refrigerant flowing through the fluid flow path in a second direction.

Referring now to FIGS. 1-3, a flow chart for a method of refrigerant delivery from a low-pressure, native refrigerant source to a cryotherapy device is shown in FIG. 1 and schematic representations of a refrigerant delivery system are shown in FIGS. 2 and 3, a schematic representation of a refrigerant delivery system is shown, the refrigerant delivery system 10 including a low-pressure refrigerant source 12 in fluid communication with a pressurization system 14 and a cryotherapy system 16. The low-pressure refrigerant source 12 may generally include a volume of refrigerant stored in a low-pressure environment within or at a medical facility 18, the pressurization system 14 may generally include a first refrigerant reservoir 20, a compressor 22, and a condenser 24, and the cryotherapy system 16 may generally include a console 28, a cryotherapy device 30. The refrigerant delivery system 10 may also include a second refrigerant reservoir 34, although this reservoir 34 may be considered to be part of the pressurization system 14 or the cryotherapy system 16, depending on the configuration of the pressurization system 14.

The pressurization system 14 may further include one or more processors 38 in communication with various components of the pressurization system 14 and, optionally, with the low-pressure refrigerant source 12 and/or the cryotherapy system 16. For example, the pressurization system 14 may include one or more processors 38 that are capable of transmitting, receiving, and/or processing data for system monitoring and control. As a non-limiting example, the pressurization system 14 may include one or more processors 38 for the automatic or semi-automatic control of the pressurization system 14, such as automatic or semi-automatic control of system valves. For simplicity, a processor 38 is shown in the figures as generally being in communication with the pressurization system 14, although it will be understood as noted above that the one or more processors 38 may be in communication with one or more specific components of the low-pressure refrigerant source 12, the pressurization system 14, and/or the cryotherapy system 16.

The first refrigerant reservoir 20 may be in fluid communication with a medical facility's refrigerant source. The term "medical facility" may refer to any facility that includes a source of refrigerant, including hospitals, walk-in clinics, and other facilities. Although a cryotherapy system 16 may be used in medical facilities, it will be understood that the method shown and described herein of pressurizing a refrigerant source for delivery to a given device may be adapted for use in other industries in addition to the medical industry.

Hospitals and other medical facilities commonly include a source of refrigerant, such as nitrous oxide ($N_2O$), that is stored as a gas at a normal working pressure of, for example, approximately 50 psig. Although different medical facilities may use various storage methods, a typical scheme is to store the gaseous $N_2O$ in large tanks connected to a manifold, which regulates the pipeline pressure to the normal working pressure (for example, approximately 50 psig). The $N_2O$ pipeline may be connected or connectable to any of a variety of medical systems and/or devices. Although this low-pressure source of refrigerant (which may also be referred to herein as a "native source of refrigerant" or "native source of $N_2O$") may provide an easily accessible supply of $N_2O$ for a cryotherapy procedure, the low-pressure $N_2O$ may have to be pressurized and liquefied before can be used in a cryotherapy system 16, a process that is discussed in more detail below.

The method shown in FIG. 1 may generally include two phases: Phase I in which a gaseous, low-pressure refrigerant is cooled and liquefied and stored in a first refrigerant reservoir 20 and Phase II in which the liquefied refrigerant is warmed and pressurized to facilitate movement of the refrigerant from the first refrigerant reservoir 20 to a second refrigerant reservoir 34.

In the first step 110 of the method, in Phase I, a gaseous refrigerant from a low-pressure refrigerant source 12 may pass along a first fluid flow path 44 to the first refrigerant reservoir 20 of the pressurization system 14. The first fluid flow path 44 may be a closed-loop flow path. As is discussed above, the low-pressure refrigerant source 12 may be a native source of refrigerant, such as $N_2O$, located within a medical facility. The first fluid flow path 44 may include one or more valves 48 for metering flow of the refrigerant from the low-pressure refrigerant source 12 to the first refrigerant reservoir 20. Although the first refrigerant reservoir 20 may be of any size, shape, and configuration, it may, for example, have a cylindrical shape with a fluid inlet 50 at a first end and a fluid outlet 52 at a second end.

Once the refrigerant is transferred from the low-pressure refrigerant source 12 to the first refrigerant reservoir 20, the temperature of the refrigerant may then be reduced in order to liquefy the gaseous refrigerant in the second step 120 of the method. Liquefying the gaseous refrigerant may reduce the pressure of the refrigerant, thereby allowing a greater amount of refrigerant to be stored within the first refrigerant reservoir 20. Refrigerant may continue to be added to the first refrigerant reservoir 20 until a pressure of the liquid refrigerant within the first refrigerant reservoir 20 becomes equalized with a pressure of the gaseous refrigerant upstream of the first refrigerant reservoir 20. To monitor pressure equalization, one or more pressure, temperature, or other sensors 56 may be included in the low-pressure refrigerant source 12, the first refrigerant reservoir 20, and/or within the first fluid flow path 44 between the low-pressure refrigerant source 12 and the first refrigerant reservoir 20. During Phase I, one or more valves 48A between the first refrigerant reservoir 20 and the second refrigerant reservoir 34 may be closed so that refrigerant cannot flow into the second refrigerant reservoir 34.

The first refrigerant reservoir 20 may be in a thermal exchange relationship with a first thermal exchange device 60. As a non-limiting example, the first thermal exchange device 60 may be an evaporator having have a coiled configuration and may be wrapped one or more times about a circumference of the first refrigerant reservoir 20. The first refrigerant reservoir 20 and the first thermal exchange device 60 may together be located within an insulating container 62. The insulating container 62 may be at least partially composed of a material or layers of materials that prevent or reduce the transmission of heat. Additionally, the insulating container 62 may be filled with, and the first thermal exchange device 60 and the first refrigerant reservoir 20 may be surrounded by, a nonfreezing liquid 64 such as methanol, propylene glycol, or other liquid having similar properties. The nonfreezing liquid 64 may improve heat transfer between the first thermal exchange device 60 and the first refrigerant reservoir 20. Thus, the first thermal exchange device 60 may cool the refrigerant within the first refrigerant reservoir 20 and the insulating container 62 may improve cooling efficiency. The insulating container 62 may have a shape and configuration similar to that of the first refrigerant reservoir 20, and may be sized just large enough to accommodate the first refrigerant reservoir 20, first thermal exchange device 60, and nonfreezing liquid 64 therein. Further, the first refrigerant reservoir 20 optionally may be integrated within the insulating container 62.

In order to reduce the temperature of the refrigerant within the first refrigerant reservoir 20 with the first thermal exchange device 60, a secondary refrigerant may be circulated through the first thermal exchange device 60. This secondary refrigerant may flow through a second fluid flow path 70 that is different than the first fluid flow path 44 of the refrigerant from the low-pressure refrigerant source 12 to the cryotherapy system 16. Put simply, the circulation of the secondary refrigerant within the second fluid flow path 70 may operate to selectively cool or warm refrigerant within the first fluid flow path 44. The secondary refrigerant may be a refrigerant that has an evaporation temperature of −45° C. or lower. As a non-limiting example, the secondary refrigerant may be R508B or R23. From the first thermal exchange device 60, the gaseous secondary refrigerant may flow through a second fluid flow path 70 and through a reversing or four-way valve 74. As is described in more detail below, operation of the reversing valve 74 may allow for the selective cooling (when in a standard-flow configuration, shown in FIG. 2) or warming (when in a reverse-flow configuration, shown in FIG. 3) of the refrigerant within the first refrigerant reservoir 20.

While still in Phase I, the gaseous secondary refrigerant may pass from the reversing valve 74 to the compressor 22. The compressor 22 may be, for example, a hermetic (also referred to as a "hermetically sealed") compressor that is configured to compress the secondary refrigerant, thereby increasing the pressure and temperature, and decreasing the volume, of the secondary refrigerant. The compressed secondary refrigerant may then pass from the compressor 22 and back through the reversing valve 74 to a first three-way valve 76. When the pressurization system 14 is in the standard-flow configuration, the first three-way valve 76 may be configured such that the secondary refrigerant flows from the reversing valve 74 to the condenser 24, such as a forced-air condenser. The condenser 24 may condense the secondary refrigerant, thereby reducing the temperature of and liquefying the high-pressure secondary refrigerant.

From the condenser 24, the secondary refrigerant may pass through a second three-way valve 78. When the pressurization system 14 is in the standard-flow configuration, the second three-way valve 78 may be configured such that secondary refrigerant passes from the condenser 24 to a filter-dryer 80. The filter-dryer 80 may be, for example, a moisture separator, a desiccant dryer, or the like. From the filter-dryer 80, the secondary refrigerant may pass through a metering device, such as an expansion valve 84. The flow of the liquid secondary refrigerant into the first thermal exchange device 60 may be metered by the expansion valve 84 such that the secondary refrigerant evaporates within the first thermal exchange device 60 and becomes a cold gas. The gaseous secondary refrigerant then may pass from the expansion valve 84 back to the first thermal exchange device 60. As discussed above, the secondary refrigerant within the first thermal exchange device 60 may reduce the temperature of the refrigerant within the first refrigerant reservoir 20. Once the first refrigerant reservoir 20 is full of refrigerant (that is, once a pressure within the first refrigerant reservoir 20 becomes equalized with a pressure of the refrigerant upstream of the first refrigerant reservoir 20), Phase II of the method may begin.

In Phase II, refrigerant from the first refrigerant reservoir 20 may be transferred to the second refrigerant reservoir 34. The second refrigerant reservoir 34 may be in thermal communication with a second thermal exchange device 86, and both may be included in the pressurization system 14. Alternatively, the second thermal exchange device 86 may be included in the pressurization system 14, and the second thermal exchange device 86 may be configured such that it can be placed in thermal exchange with a second refrigerant reservoir 34 that is included in the cryotherapy system 16. Alternatively, the second refrigerant reservoir 34 and the second thermal exchange device 86 may both be a part of the cryotherapy system 16. In this case, the second fluid flow path 70 of the pressurization system 14 may be configured to be fluidly connected to one or more components of the cryotherapy system 16, such as the second thermal exchange device 86 in thermal exchange with the second refrigerant reservoir 34. The second refrigerant reservoir 34 may be sized and configured to fit within the cryotherapy system console 28, although the second refrigerant reservoir 34 may alternatively be located outside the console 28. Thus, although the second refrigerant reservoir 34 is shown in FIGS. 2 and 3 as being located outside of the console 28 for simplicity, it will be understood that the second refrigerant reservoir 34 may instead be located within the console 28.

It will be understood that the pressurization system 14 may be a kit that is adapted to be connected to both a low-pressure refrigerant source 12, such as a native nitrous oxide source at a hospital or other medical facility, and a cryotherapy system 16, including the cryotherapy system console 28 and device 30. For example, the pressurization system 14 may include one or more sensors for monitoring system parameters, such as temperature and pressure. Data collected by these one or more sensors 56 may be communicated to the pressurization system processor 38 and/or the cryotherapy system console 28. Further, the pressurization system 14 processor may be in communication with the cryotherapy system console 28 to exchange data. For example, the pressurization system processor 38 may send a signal to the cryotherapy system console 28 when the second refrigerant reservoir 34 is full and sufficiently cooled for commencement of a cryotherapy procedure. Further, the pressurization system 14 processor may enable the automatic or semi-automatic control of the pressurization system 14, such as automatic or semi-automatic control of the reversing valve 74, expansion valve 84, and the first 76 and second 78 three-way valves.

In the third step 130 of the method, in Phase II, the temperature of the refrigerant within the first refrigerant reservoir 20 may be increased or allowed to increase in order to facilitate transfer of the refrigerant to the second refrigerant reservoir 34. For example, the flow of the secondary refrigerant within the second fluid flow path 70 may be discontinued in order to allow the temperature, and therefore the pressure, of the refrigerant within the first refrigerant reservoir 20 to gradually increase. As a non-limiting example, the temperature of the refrigerant may be allowed to increase to a temperature that is slightly higher than ambient temperature, such as approximately 30° C. (±5° C.) and the pressure may be allowed to increase to approximately 900 PSI (±50 PSI). At the same time, the temperature of the pressurized refrigerant may be reduced as it is transferred to the second refrigerant reservoir 34.

Additionally or alternatively, the pressurization system 14 may include one or more valves that may increase the rate at with the pressure and temperature of the refrigerant within the first fluid is increased. For example, the reversing valve 74 of the pressurization system 14 may reverse the flow of the secondary refrigerant through the second fluid flow path 70. In Phase II, before the refrigerant is transferred from the first refrigerant reservoir 20 into the second refrigerant reservoir 34, flow of the secondary refrigerant may be reserved such that the temperature of refrigerant within the first refrigerant reservoir 20 is increased and the temperature of the refrigerant within the second refrigerant reservoir 34 as decreased.

In this reverse-flow configuration (shown in FIG. 3), secondary refrigerant may pass through the second fluid flow path 70 through the compressor 22. Warmed from the compressor 22, the secondary refrigerant may then pass to the first thermal exchange device 60, which may function like a condenser in the reverse-flow configuration because of the low-temperature condition of the refrigerant within the first refrigerant reservoir 20 created in Phase I. As a result, the secondary refrigerant may be liquefied within the first thermal exchange device 60. Due to the thermal exchange relationship between the first thermal exchange device 60 and the first refrigerant reservoir 20, the refrigerant within the first refrigerant reservoir 20 may increase whereas the temperature of the secondary refrigerant within the first thermal exchange device 60 may decrease.

The cooled secondary refrigerant may pass from the first thermal exchange device 60 through the expansion valve 84 and the filter-dryer 80, and then through the second three-way valve 78. When the pressurization system 14 is in the reverse-flow configuration, the second three-way valve 78 may be configured such that the secondary refrigerant bypasses the condenser 24 and instead passes from the filter-dryer 80 into the second thermal exchange device 86 that is in a thermal exchange relationship with the second refrigerant reservoir 34. The liquid secondary refrigerant may evaporate within the second thermal exchange device 86 and, by virtue of the thermal exchange relationship, may cool the refrigerant within the second refrigerant reservoir 34. In some configurations, the second thermal exchange device 86 may be included in the cryotherapy system console 28 and may be in thermal exchange with the second refrigerant reservoir 34. The pressurization system 14 may be configured to be in fluid communication with existing cryotherapy systems, such as by using one or more connectors, valves, or other after-market components to connect the two systems.

Secondary refrigerant may then pass from the second thermal exchange device 86 to the first three-way valve 76. In the reverse-flow configuration, the first three-way valve 76 may be configured such that the secondary refrigerant flows from the second thermal exchange device 86 to the reversing valve 74 and then to the compressor 22. Secondary refrigerant may then pass from the compressor 22 back into the first thermal exchange device 60 within the insulating container 62.

The circulation of the secondary refrigerant through the second fluid flow path 70 in the reverse-flow configuration may be discontinued once no flow is circulating through the valve 48 just upstream of the second refrigerant reservoir 34 or once a certain refrigerant level is reached inside the first refrigerant reservoir 20.

In the fourth step 140 of the method, in Phase II, the refrigerant may be transferred from the first refrigerant reservoir 20 to the second refrigerant reservoir 34. In the fourth step 140, one or more valves 48A between the first refrigerant reservoir 20 and the second refrigerant reservoir 34 may be fully or partially open to allow the refrigerant to flow from the first refrigerant reservoir 20 to the second refrigerant reservoir 34. To further facilitate the transfer, the first fluid flow path 44 may include a vacuum source 90 that creates a pressure differential within the first fluid flow path 44. In this way, refrigerant may be drawn by the vacuum source 90 from the first refrigerant reservoir 20 to the second refrigerant reservoir 34. Once the refrigerant is within the second refrigerant reservoir 34, the refrigerant may be circulated through a cryotherapy device 30 used to perform a cryotherapy procedure, such as cardiac ablation and/or mapping. Circulation of the secondary refrigerant within the second fluid flow path 70 may continue in the reverse-flow configuration during at least a part of the cryotherapy procedure, in order to maintain the pressurized refrigerant at a low temperature within the second refrigerant reservoir 34.

It will be understood that the medical facility, pressurization system 14, and/or the cryotherapy system 16 may include system components in addition to those shown in the figures, such as one or more valves, computers, processors, fluid reservoirs, user input devices, sensors, vacuum sources, power generators, or the like. Although not shown, the pressurization system 14 may include one or more temperature sensors and/or pressure sensors located throughout the system for monitoring fluid temperature within the first and/or second fluid flow path 70. Additionally, the pressurization system 14 and/or the cryotherapy system 16 may include one or more displays, audio alerts, visual alerts, or the like for communicating system conditions to a user. Further, it will be understood that although each of the second fluid flow path 70 components of the pressurization system 14 may include an inlet port and an outlet port, whether each port functions as an inlet or an outlet may be determined by whether the second fluid flow path 70 is operating in the standard-flow configuration or the reverse-flow configuration.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A kit for pressurizing low-pressure refrigerant, the kit comprising:
   a first fluid reservoir;
   a second fluid reservoir in fluid communication with the first fluid reservoir;
   a closed-loop fluid flow path including:
      a first thermal exchange device in thermal communication with the first fluid reservoir;
      a second thermal exchange device in thermal communication with the second fluid reservoir;
      a reversing valve, the reversing valve being configured to selectively allow flow of a secondary refrigerant within the closed-loop fluid flow path in a first direction and flow of the secondary refrigerant within the closed-loop fluid flow path in a second direction;
      a compressor in fluid communication with the first thermal exchange device and the second thermal exchange device; and
      a condenser that is:
         in fluid communication with the first thermal exchange device and the second thermal exchange device when the reversing valve allows flow of the secondary refrigerant within the closed-loop fluid flow path in the first direction; and
         in fluid communication with the first thermal exchange device and fluidly isolated from the second thermal exchange device when the reversing valve allows flow of the secondary refrigerant within the closed-loop fluid flow path in the second direction.

2. The kit of claim 1, wherein flow of the secondary refrigerant within the closed-loop fluid flow path in the first direction decreases a temperature of low-pressure refrigerant within the first fluid reservoir and an increase in a temperature of pressurized refrigerant within the second fluid reservoir.

3. The kit of claim 1, wherein flow of the secondary refrigerant within the closed-loop fluid flow path in the second direction increases a temperature of low-pressure refrigerant within the first fluid reservoir and a decrease in a temperature of pressurized refrigerant within the second fluid reservoir.

4. The kit of claim 1, wherein flow of the secondary refrigerant within the closed-loop fluid flow path in the second direction increases a pressure of low-pressure refrigerant within the first fluid reservoir to transform the low-pressure refrigerant to a pressurized refrigerant.

5. The kit of claim 1, wherein the kit is connectable to a cryotherapy system.

6. The kit of claim 5, wherein the kit is further connectable to a native source of low-pressure refrigerant, the kit being configured to receive low-pressure refrigerant from the native source and to deliver pressurized refrigerant to the cryotherapy system.

7. The kit of claim 1, wherein the first thermal exchange device is coiled around at least a portion of the first fluid reservoir.

8. The kit of claim 1, wherein the second thermal exchange device is coiled around at least a portion of the second fluid reservoir.

9. The kit of claim 1, wherein the first fluid reservoir and the first thermal exchange device are within an insulating container and immersed within a liquid including methanol, propylene glycol, or other liquid having similar properties.

10. The kit of claim 1, further comprising:
    an expansion valve located between the condenser and the first thermal exchange device.

11. The kit of claim 10, wherein the expansion valve is configured to meter the flow of the secondary refrigerant from the condenser to the first thermal exchange device such that the secondary refrigerant evaporates within the first thermal exchange device.

12. The kit of claim 10, further comprising:
    a first three-way valve located between the reversing valve and the condenser, the first three-way valve being configured to transfer the secondary refrigerant:
       from the compressor to the condenser when the reversing valve allows flow of the secondary refrigerant within the closed-loop fluid flow path in the first direction; and
       from the second thermal exchange device to the compressor when the reversing valve allows circulation of the secondary refrigerant within the closed-loop fluid flow path in the second direction; and
    a second three-way valve located between the condenser and the expansion valve, the second three-way valve being configured to transfer the secondary refrigerant:

from the condenser to the expansion valve when the reversing valve allows flow of the secondary refrigerant within the closed-loop fluid flow path in the first direction; and from the expansion valve to the second thermal exchange device when the reversing valve allows circulation of the secondary refrigerant within the closed-loop fluid flow path in the second direction.

\* \* \* \* \*